United States Patent [19]

Jain

[11] 4,317,812

[45] Mar. 2, 1982

[54] **POLYNITROXIN ANTIBIOTICS PRODUCED BY *NOCARDIOPSIS MUTABILIS* SHEARER SP. NOV. ATCC 31520**

[75] Inventor: Tikam C. Jain, King of Prussia, Pa.

[73] Assignee: SmithKline Corporation, Philadelphia, Pa.

[21] Appl. No.: 225,156

[22] Filed: Jan. 15, 1981

[51] Int. Cl.³ .............................................. A61K 35/00
[52] U.S. Cl. ..................................... 424/116; 435/170
[58] Field of Search ......................... 424/116; 435/170

[56] References Cited

U.S. PATENT DOCUMENTS 3,925,546  12/1975  Shimojima et al. ................. 424/116

*Primary Examiner*—Jerome D. Goldberg
*Attorney, Agent, or Firm*—Joseph F. DiPrima; Richard D. Foggio; Alan D. Lourie

[57] ABSTRACT

A novel antibiotic, polynitroxin, is produced by the cultivation of a fermentation broth containing *Nocardiopsis mutabilis* Shearer sp. nov. ATCC 31520 in an aqueous nutrient medium under submerged aerobic conditions.

9 Claims, 3 Drawing Figures

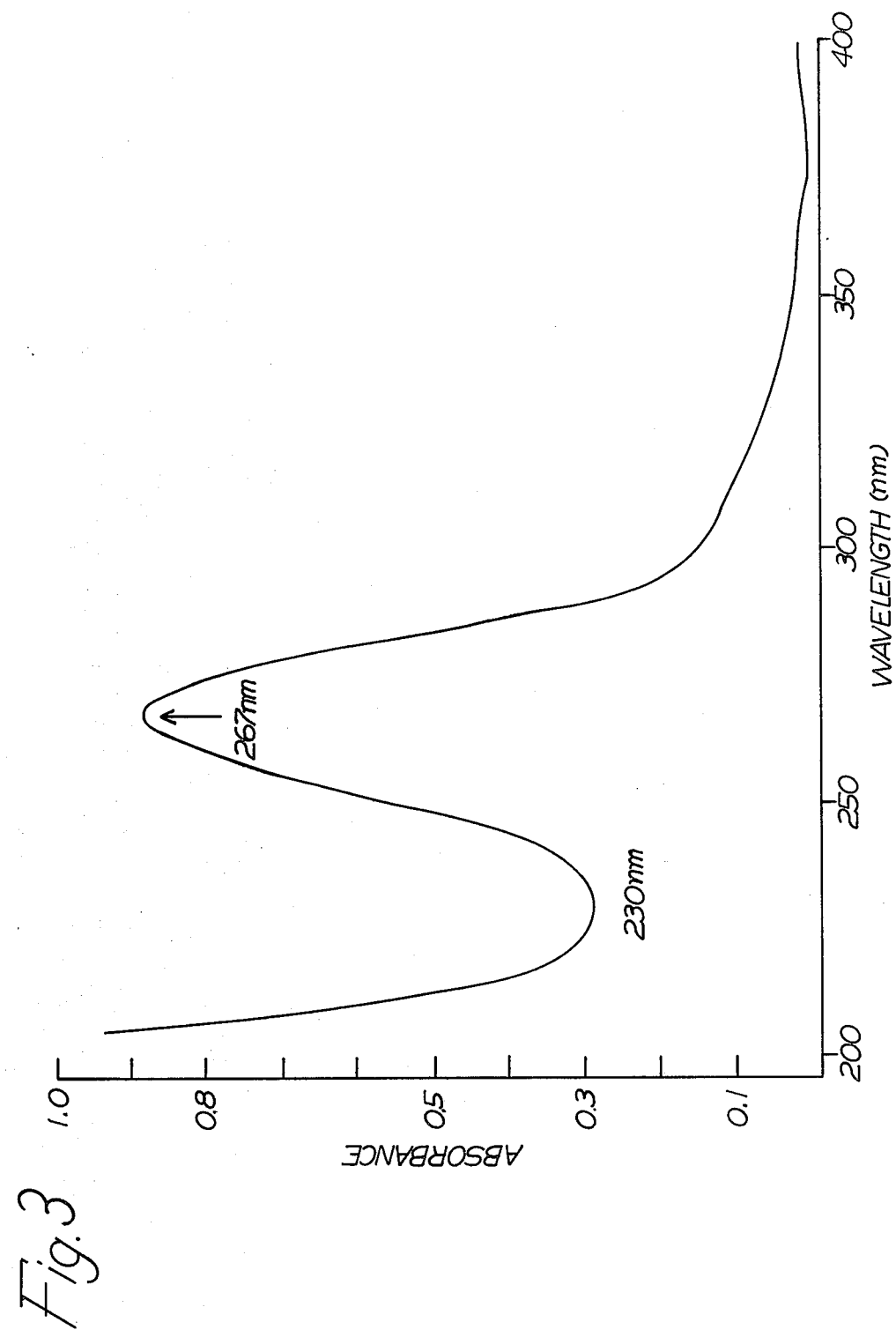

POLYNITROXIN ANTIBIOTICS PRODUCED BY *NOCARDIOPSIS MUTABILIS* SHEARER SP. NOV. ATCC 31520

SUMMARY OF THE INVENTION

This invention relates to new polynitroxin antibiotics and the production and recovery thereof. More particularly, this invention relates to the antibiotic, designated herein polynitroxin, said compound being produced by cultivating *Nocardiopsis mutabilis* Shearer sp. nov. ATCC 31520 in an aqueous nutrient medium containing assimilable sources of nitrogen and carbon, under submerged aerobic conditions until a substantial amount of the polynitroxin antibiotic is produced by the microorganism in said culture medium and optionally, recovering polynitroxin from the culture medium.

DETAILED DESCRIPTION

The new antibiotic, polynitroxin, is produced by the fermentation of a new member of the genus Nocardiopsis, designated *Nocardiopsis mutabilis* Shearer sp. nov. SK&F-AAA025. The above-noted microorganism was obtained from a soil sample collected in a cultivated field located on the way to Visanagar in Gujarat, India. A culture of the microorganism has been deposited in the American Type Culture Collection, Rockville, Md. as the type culture under accession no. ATCC 31520.

Figure 1:
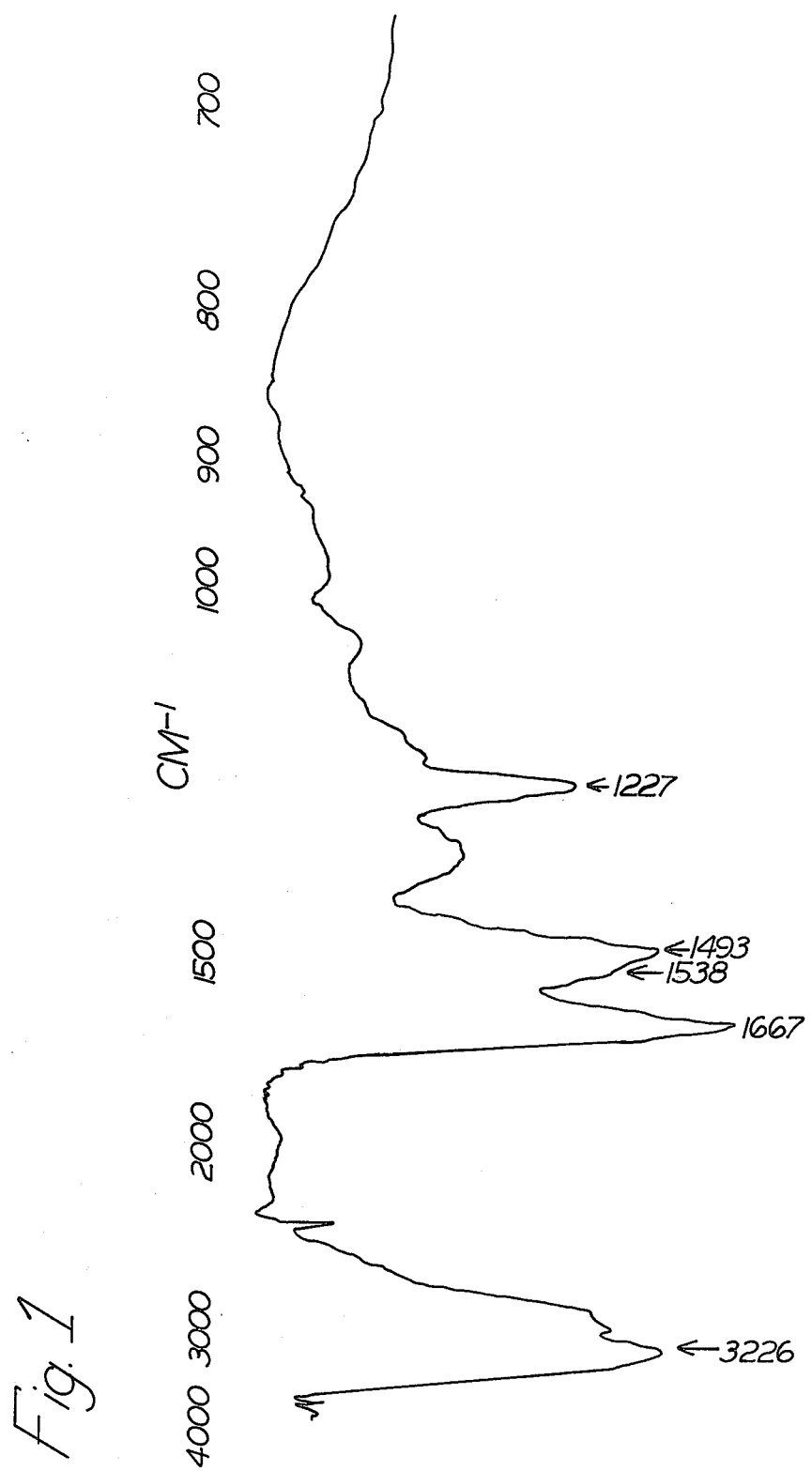
Figure 2:
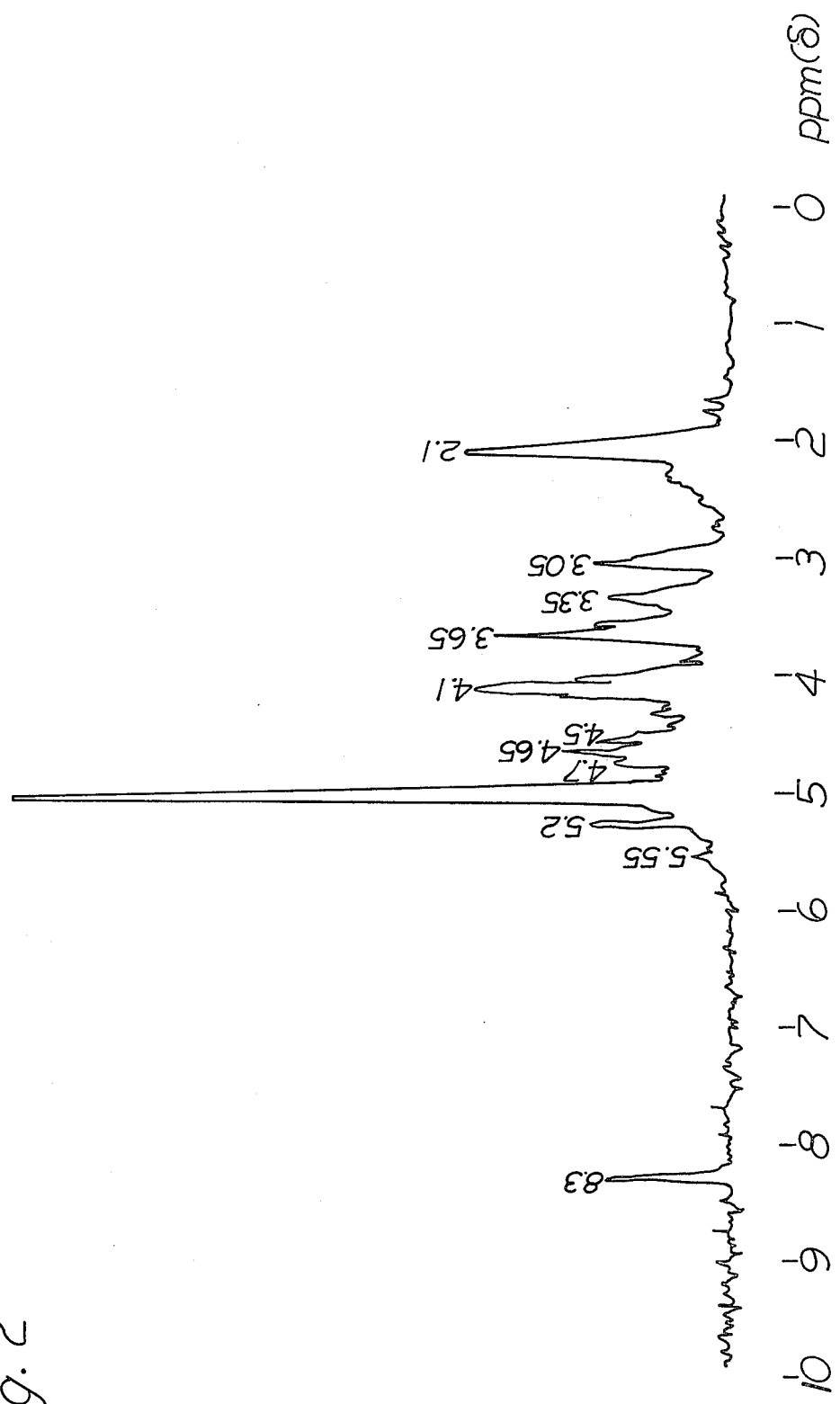

The fermentation of *Nocardiopsis mutabilis* Shearer sp. nov. ATCC 31520 results in the production of a polynitroxin antibiotic. The polynitroxin antibiotic in the form of the hydrochloride salt has the following characteristics:

(a) a melting point of 255°–258° C. (dec.);

(b) an approximate elemental composition of 33.32 percent carbon, 6.22 percent hydrogen, 21.49 percent nitrogen and 15.81 percent chlorine;

(c) an infrared absorption spectrum in potassium bromide which exhibits peaks at the following wavenumbers in $cm^{-1}$: 3226, 1667, 1538, 1493 and 1227 as shown in FIG. 1;

(d) a nuclear magnetic resonance spectrum (Fourier Transform) in deuterium oxide which exhibits the following chemical shifts in ppm: 8.3, 5.55, 5.2, 4.65 (m), 4.1 (t), 3.65 (d), 3.35, 3.05 and 2.1 as shown in FIG. 2;

(e) an ultraviolet absorption spectrum in water which exhibits an absorption maximum at 267 nm and an absorption minimum at 230 nm as shown in FIG. 3;

(f) a specific rotation $[\alpha]_D^{25} = -22.2°$ (C, 1.0 in $H_2O$); and (g) positive reactions with ninhydrin, molybdate, and permanganate and a negative reaction with periodate.

It should be noted the ultraviolet absorption spectrum of polynitroxin hydrochloride in acidic aqueous medium exhibits an absorption maximum at 267 nm and an absorption minimum at 230 nm which are identical to those under neutral conditions. However, under basic conditions the absorption maximum and minimum of the ultraviolet absorption spectrum is 285 nm and 240 nm, respectively.

The crystalline hydrochloride of polynitroxin was hydrolyzed with 6N-hydrochloric acid to afford, after purification, orotic acid. The identification of the hydrolysis product as orotic acid was established by comparing the mass spectrum fragmentation pattern, the ultraviolet absorption spectrum and the paper chromatograph of an authentic sample of orotic acid with those of the hydrolysis product.

The absence of uracil, thymine, 5-hydroxymethyluracil, and uracil-5-carboxylic acid in the hydrolysate has been established by thin layer chromatography, paper chromatography, high pressure liquid chromatography, ultraviolet absorption spectra, and mass spectra.

THE MICROORGANISM

*Nocardiopsis mutabilis* Shearer sp. nov. SK&F-AAA025 (ATCC 31520) is an aerobic, gram-positive, not acid fast, catalase positive organism that produces no melanoid pigments. Purified cell wall preparations of SK&F-AAA025, analyzed by the methods of Becker [Becker et al., Appl. Microbiol. 13, 236–43 (1965)], contained the meso-isomer of 2,6-diaminopimelic acid along with alanine, glutamic acid, glucosamine and muramic acid; no diagnostically important sugars were present. Whole-cell hydrolysates, analyzed by the method of Becker [Becker et al., Appl. Microbiol. 12, 421–23 (1964)], contained galactose, glucose, mannose, ribose, and rhamnose but no madurose. No mycolic acids of any type were present in cell extracts analyzed for lipid patterns by the methods of Lechevalier [Lechevalier et al., J. Bacteriol. 105, 313–18 (1971)]. In phospholipid analyses, carried out by the methods of Lechevalier [Lechevalier et al., Biochem. System. Ecol. 5, 249–60 (1977)], the phospholipids found were cardiolipin, lysocardiolipin, phosphatidyl ethanolamine, phosphatidyl inositol, diphosphatidyl glycerol and unknown glucosamine-containing phospholipids. Thus SK&F-AAA025 has a type III cell wall with a whole cell sugar pattern of type C [Lechevalier et al., Int. J. Syst. Bacteriol. 20, 435–43 (1970)] and a phospholipid type of PIV [Lechevalier et al., Biochem. System. Ecol. 5, 249–60 (1977)].

*N. mutabilis* forms a distinct mycelium; the vegetative mycelium is well-developed with hyphae that are long and branched and fragment into coccobacillary units in four to seven days. The aerial mycelium consist of long, moderately branching hyphae which are straight or irregularly curved and completely fragment into spores. The spores are smooth walled and elongated.

The description of *N. mutabilis* on various media follows. All cultures were incubated at 28° C. in the dark and observed for twenty-one days. The colors for the culture were chosen by comparison with chips from the ISCC-NBS Centroid Color Charts.

Yeast-Extract-Malt Extract Agar—growth excellent, raised and wrinkled; vegetative mycelium-yellow (ISCC-NBS 89, pale yellow); reverse-yellow brown; aerial mycelium-abundant (ISCC-NBS 263, white); no soluble pigment present.

Inorganic Salts-Starch Agar—growth good; vegetative mycelium-yellow (ISCC-NBS 82, very yellow); reverse-yellow brown; aerial mycelium-abundant but thin (ISCC-NBS 263, white); light brown soluble pigment present.

Oatmeal Agar—growth fair to good; vegetative mycelium-yellow (ISCC-NBS 89, pale yellow); reverse-yellow brown; aerial mycelium-abundant but thin (ISCC-NBS 263, white); no soluble pigment present.

Glycerol Asparagine Agar—growth good; vegetative mycelium-yellow (ISCC-NBS 67, brilliant orange yellow); reverse-yellow brown; aerial mycelium-abundant but thin (ISCC-NBS 263, white); light brown soluble pigment present.

M172 Agar—growth excellent, raised and wrinkled; vegetative mycelium-yellow (ISCC-NBS 72, dark orange yellow); reverse-yellow brown; aerial mycelium-moderate (ISCC-NBS 263, white); yellow brown soluble pigment present.

Soil Extract Agar—growth fair, flat; vegetative mycelium-yellow (ISCC-NBS 89, pale yellow); reverse-pale yellow brown; aerial mycelium-abundant but thin (ISCC-NBS 263, white); no soluble pigment present.

Tyrosine Agar—growth good; vegetative mycelium-yellow (ISCC-NBS 86, light yellow); reverse-yellow brown; aerial mycelium-abundant (ISCC-NBS 263, white); no soluble pigment present.

Defined Agar–growth good, raised and wrinkled; vegetative mycelium-yellow (ISCC-NBS 71, moderate orange yellow); reverse-yellow brown; aerial mycelium-none to sparse (ISCC-NBS 263, white); yellow brown soluble pigment present.

Glucose-Yeast Extract Agar—growth good, raised and wrinkled; reverse-yellow brown; aerial mycelium-none to sparse; light yellow brown soluble pigment present.

Nutrient Agar—growth fair, thin; reverse-light yellow brown; aerial mycelium-sparse, thin, white; no soluble pigment present.

Czapek-Sucrose Agar—growth fair, flat; reverse-light yellow brown; aerial mycelium-sparse, thin, white; light yellow brown soluble pigment present.

Thin Potato Carrot Agar—growth fair to good; reverse-yellow brown; aerial mycelium-abundant but thin, white; no soluble pigment present.

Stock cultures of *N. mutabilis* were grown on Medium 172 at 28° C. The physiological tests employed in characterizing the culture were those of Gordon [Gordon, J. Gen. Microbiol. 45 355-64 (1966)] and Gordon and Mihm [Gordon et al., Ann. N.Y. Acad. Sci. 98, 628-36 (1962)]. All plate media were observed for 21 days and tubed media were observed for 28 days.

The biochemical and physiological characteristics of *N. mutabilis* are as follows.

No growth takes place under anaerobic conditions. The temperature range for growth is 15° C. to 45° C. No growth occurs at 10° C. or 50° C. Starch, casein, L-tyrosine, and hypoxanthine are hydrolyzed but adenine, xanthine, and urea are not. Nitrate is reduced to nitrite. Growth occurs in lysozyme broth. Milk is peptonized. Gelatin is both hydrolyzed and liquified. No hydrogen sulfide or melanoid pigments are produced. Esculin is decomposed; catalase is produced. Acid is produced from dextrose, raffinose, melibiose, D-arabinose, L-arabinose, D-cellobiose, D-ribose, D-fructose, D-galactose, glycerol, i-inositol, lactose, D-mannose, D-melezitose, salicin, soluble starch, sacrose, trehalose, D-xylose, dextrin, glycogen, maltose, α-methyl-D-glucoside, and α-methyl-D-mannoside. No acid is produced from adonitol, dulcitol, inulin, D-mannitol, rhamnose, D-sorbitol, L-sorbose, and i-erythritol. Citrate, malate, succinate, acetate, pyruvate, lactate and propionate are utilized; formate, oxalate, benzoate and tartrate are not utilized.

The above-described microorganism has the characteristics of a nocardioform organism and is placed in the genus of Nocardiopsis. Its description, however, does not agree with any known species of Nocardiopsis and is hereby described as new under the name *Nocardiopsis mutabilis* Shearer sp. nov. SK&F-AAA025. The specific epithet refers to the variety of colony morphology observed on rich organic media.

PREPARATION OF POLYNITROXIN ANTIBIOTICS

Polynitroxin antibiotics may be produced by cultivating a strain of Nocardiopsis having the characteristics of ATCC 31520 or a mutant thereof under submerged aerobic conditions in an aqueous nutrient medium. The organism is grown in a nutrient medium containing an assimilatable carbon source, for example an assimilable carbohydrate. Examples of suitable carbon sources include sucrose, lactose, maltose, mannose, fructose, glucose, and soluble starch. The nutrient medium should also contain an assimilatable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the polynitroxin antibiotics can be effected at any temperature conducive to satisfactory growth of the organism, e.g., 20°–45° C., and is conveniently carried out at a temperature from 20° to 32° C., but preferably at 28° C.

The medium normally is neutral, but the exact pH can be varied between 5.0 and 7.5 depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the vegetative cells of the organism. After obtaining an inoculum in this manner, it is transferred aseptically to the fermentation tank medium for large scale production of the antibiotics. The medium used for the vegetative inoculum can be the same as that employed for larger fermentations, although other media can be employed.

As is customary in aerobic submerged culture processes, sterile air is sparged through the culture medium. Agitation may be maintained by means of agitators generally familiar to those in the fermentation industry.

In general, optimum production of the antibiotic is achieved after incubation periods of about 72–196 hours in stir-jar fermentors or tank fermentors. (The fermentation can be followed by assaying the fermentation medium from time to time against a susceptible organism, e.g. *Staphylococcus aureus* 209 P, *Escherichia coli* SS or *Escherichia coli* K802N.)

The crude antibiotic may be recovered from the fermentation medium by treating the clarified broth with an ion exchange resin (IRC-50 in the H+ form) followed by elution with a water-0.5 N hydrochloric acid gradient. The active fractions were neutralized with an ion exchange resin (IRA-68) to afford the crude antibiotic.

PURIFICATION OF POLYNITROXIN

The crude polynitroxin antibiotic may be purified by fractionation on an activated carbon column by eluting said column with 75% aqueous acetone containing a trace of hydrochloric acid. The active material recovered from the column may be absorbed onto an ion exchange resin (IRC-50 in the H+ form) which is then eluted with 0.1 N hydrochloric acid. The active fractions were combined and lyophilized to give a whitish brown solid which after several crystallizations from aqueous methanol gave the pure polynitroxin antibiotic in the hydrochloride form.

BIOLOGICAL ACTIVITY DATA

A purified sample of polynitroxin in the hydrochloride form gave the following minimum inhibitory concentration (MIC).

| MIC of Polynitroxin Hydrochloride | |
|---|---|
| Test Organisms | μg/ml |
| *Staphylococcus aureus* HH127 | 250 |
| *Staphylococcus aureus* SA910 | >250 |
| *Streptococcus faecalis* HH 34358 | >250 |
| *Proteus mirabilis* PM 444 | 250 |
| *Escherichia coli* 12140 | 63 |
| *Klebsiella pneumoniae* SKF 4200 | 31 |
| *Salmonella gallinarum* ATCC 9184 | 31 |
| *Pseudomonas aeruginosa* HH 63 | 125 |
| *Serratia marcescens* ATCC 13880 | 125 |
| *Proteus morganii* P179 | 125 |
| Providencia sp. PR-276 | 125 |
| *Enterobacter cloacae* HH 31254 | 63 |

A crude sample of the polynitroxin antibiotic exhibited a maximum tolerable dose in mice of 500 mg./kg. and an $ED_{50}$ of 230 mg./kg. in mice infected with *E. coli* 12140.

The antibiotic compounds of the present invention, including the crude polynitroxin, and polynitroxin as the hydrochloride salt, exhibit antibacterial activity. The invention includes within its scope pharmaceutical compositions containing at least one of the abovementioned antibiotic compounds and a pharmaceutically acceptable carrier. The compositions may also contain other active antibacterial agents. Compositions may be made up in any pharmaceutical form appropriate for the route of administration in question. Such compositions are exemplified by solid compositions for oral administration, such as tablets, capsules, pills, powders and granules; liquid compositions for oral administration, such as solutions, suspensions, syrups and elixirs; and preparations for parenteral administrations such as sterile solutions, suspensions or emulsions.

For use as an antibacterial agent, the compositions are administered so that the concentration of the active ingredient is greater than the minimum inhibitory concentration for the particular organism being treated. The antibiotic compounds of the present invention may also be used in combination with detergents as a wash solution for sanitary purposes, such as cleaning of laboratory glassware and equipment or laundering of laboratory uniforms.

The following examples are illustrative of the present invention and are not therefore to be considered in limiting the present invention as described in the claims appended hereto.

EXAMPLE 1

Shake-Tube Fermentation

Inoculum Preparation

Growth scraped from half confluent slant with 2 ml. saline.
One ml. cell suspension transferred to 10 ml. medium 13 (starch, 30 g.; sucrose, 10 g.; dextrose, 10 g.; soy peptone, 15 g.; corn steep liquor, 10 g.; $K_2HPO_4$, 3 g.; NaCl, 1 g.; $CaCO_3$, 3 g.; distilled water, 1 l. and mineral solution 10 ml.—$ZnSO_4$ $7H_2O$, 2.8 g.; $Fe(NH_4)_2C_6H_5O_7$, 2.7 g.; $CuSO_4$ $5H_2O$, 0.125 g.; $MnSO_4$, 1 g.; $CoO_2$ $6H_2O$, 0.1 g.; $Na_2B_4O_7.H_2O$, 0.09 g.; $Na_2MoO_4.2H_2O$, 0.05 g.; distilled water, 1 l.) in shake tube.

Inoculum grown for 3 days at 28° C. on reciprocal tube-shaker.

Fermentation

Ten ml. medium 31 (lactose, 30 g.; soluble starch, 10 g.; yeast extract, 5 g.; corn steep liquor, 2 g.; bacto peptone, 2 g.; fish meal, 1 g.; $CaCO_3$, 1 g.; $CoCO_3$, 1 mg.; and distilled water., 1 l.) or L-3 medium (glycerol, 35 g.; glucose, 7.5 g.; $(NH_4)_2SO_4$, 3 g.; lard water, 20 g.; NaCl, 2 g.; $CaCO_3$, 3 g.; Amber BYF, 2 g.; tap water, 1 l.) was inoculated with 1 ml. 72-hour vegetative culture.

Inoculated fermentation medium was incubated for 3 days at 28° C. on reciprocal shaker.

Activity was detected using *Escherichia coli* 12140, 427 and 430.

EXAMPLE 2

Shake-Flask Fermentation

The culture was grown in a similar fashion to that described in Example 1. The growth from a complete slant was used to inoculate 100 ml. of medium 13 in a 500 ml. Erlenmeyer flask. These cultures were grown on a rotary shaker, 250 rpm, at 28° C. for 3 days. Thirty ml. of 72-hour culture was used to inoculate 300 ml. of medium 31 or L-3 in 2 l. Erlenmeyer flask. The antibiotic was detected after 3 to 4 days at 28° C. on a rotary shaker (300 rpm).

| Microbe | | Zone Size (mm)/3 days |
|---|---|---|
| *Staphylococcus aureus* | 910 rif | 19 |
| *Staphylococcus aureus* | 209P | 15 |
| *Escherichia coli* SS | SK & F-AAA308 | 20 |
| *Escherichia coli* stn-1 | SK & F-AAA285 | 12 |
| *Escherichia coli* stn-1 | K802N | 19 |
| *Escherichia coli* stn-1 | K802N/R6 | 16 |
| *Escherichia coli* stn-1 | K802N/JR214 | 18 |

EXAMPLE 3

Tank Fermentation

The culture was grown in a similar fashion to that described in Examples 1 and 2. The growth from a complete slant was used to inoculate 1 l. of medium 13 in a 4 l. aspirator bottle. The aspirator bottle was inoculated at 28° C. on a rotary shaker (250 rpm, 2-in. throw) for 3-4 days. Growth was monitored microscopically and by packed cell volume.

About 1 l. of actively grown culture was transferred to 14 l. fermentation containing 10 l. of L-3 medium. The fermentor was operated at 28° C., with agitation rate of 300-500 rpm and aeration rate of 3-5 l./min. Foam was controlled with lard oil containing 10% PPG. The fermentation was harvested after 60-100 hours. The production of the antibiotic, polynitroxin was monitored using *S. aureus* 209P, *E. coli* SS, SK&F-AAA308 and *E. coli* K802N. Typical activities are shown below.

| Hours | Zone Size (mm)[a] | | |
|---|---|---|---|
| | S. aureus 209 P | E. coli ss | E. coli K802N |
| 18 | 0 | 0 | 0 |
| 42 | 0 | 0 | 0 |
| 66 | 12 | 13.5 | 11 |
| 90 | 17.5 | 19 | 15 |

[a] Disc diffusion assay using indicated organism at a cell density of about $10^5$–$10^7$/ml. Assay plates were incubated at 25° C. for 24 hours prior to recording zones.

EXAMPLE 4

Tank Fermentation

The culture was grown in a similar fashion to Example 3. The inoculum was developed through slants, to shake bottles and 14 l. fermentor using medium 13. An actively growing culture in 14 l. fermentor (3–4 days) was transferred to a 70 l. fermentor containing 50 l. medium L-3. This fermentor was operated at 28° C. with agitation rate of 250–300 rpm and air flow of 25–35 l./min. Foam was controlled with lard oil containing 10% PPG. The growth was monitored microscopically and by packed biomass. Production of the antibiotic, polynitroxin, was monitored using the following test strains:

| Hours | Zone Size (mm)[a] | | |
|---|---|---|---|
| | S. aureus 209P | E. coli ss | E. coli K802N |
| 18.5 | 0 | 0 | 0 |
| 42.5 | 14 | 18 | 15 |
| 66.5 | 14 | 20 | 16 |

[a] Disc diffusion assay at 25° C.

EXAMPLE 5

Isolation

Five liters of fermentation broth from Example 3 was clarified by filtration using a filter-aid and the filter cake was discarded. The clarified broth (5 l., pH 7) was run through IRC-50 (in the H+ form) in a column (resin bed 5.5×49 cm) which was then eluded with a water—0.5 N HCl gradient. Active fractions (*E. coli* SS as test strain) were neutralized with IRA-68, combined and decolorized by passing through an XE-268 column (resin bed 3×31 cm) to yield the desired polynitroxin antibiotic.

EXAMPLE 6

Isolation

Thirty-nine liters of broth from Example 4 was clarified by filtration with filter-aid. The antibiotic, polynitroxin, was absorbed onto IRC-50 (in the H+ form) and eluted with a water—0.5 N HCl gradient. The active fractions were neutralized with IRA-68, combined and freeze-dried to yield crude antibiotic.

EXAMPLE 7

Final Purification

Crude antibiotic from Example 5 was partly dissolved in water (100 ml.) and charged on a carbon (5 g.) column. Only about 50% of the material was soluble in water. The column was washed with water (2 l.) and eluted with 75% aqueous acetone (500 ml) containing a trace of HCl. The active material was recovered and absorbed onto IRC-50 (in the H+ form). The column was washed with water and eluted with 0.1 N HCl (500 ml.). Active fractions were pooled and lyophilized to give whitish-brown solid. Several crystallizations of this solid from aqueous methanol gave pure polynitroxin in the form of a hydrochloride salt, melting point 255°–258° C. (dec.).

EXAMPLE 8

Hydrolysis of Polynitroxin

Polynitroxin hydrochloride, as prepared in Example 7, (100 mg) was dissolved in 6N-hydrochloric acid (20 ml) and then heated on a steambath for 3 hours. The resultant solution was treated with an ion exchange resin (AG2-X8) in the hydroxyl form until the pH was 7.0. The solution was then concentrated and lyophilized to afford the crude hydrolysate (94 mg) as a yellow solid. The crude hydrolysate was purified by means of ion exchange resins, active carbon, and preparative paper chromatography to afford orotic acid based on the following comparison with authentic orotic acid.

| I. Mass Spectra Fragmentation 70 eV - m/e (relative intensity) | |
|---|---|
| Hydrolysis product | Orotic acid |
| 43 (21.9) | 43 (29.2) |
| 85 (5.9) | 85 (6.5) |
| 113 (0.0) | 113 (0.0) |
| 156 (0.3) | 156 (0.4) |
| 149 (10.4) | 149 (10.4) |
| 223 (0.8) | 223 (0.7) |

| II. Ultraviolet Spectra (Max) | | |
|---|---|---|
| | Hydrolysis product | Orotic acid |
| $H_2O$, pH 2 | 274 nm | 274 nm |
| $H_2O$, pH 11 | 278 nm | 279 nm |

| III. Paper Chromatography | | |
|---|---|---|
| | Hydrolysis product | Orotic acid |
| n-BuOH:HOAc:$H_2O$ (4:1:5) | $R_f$ 0.22 | $R_f$ 0.20 |

What is claimed is:

1. A polynitroxin antibiotic which in the form of the hydrochloride salt is characterized as follows:
   (a) a melting point of 255°–258° C. (dec.);
   (b) an approximate elemental composition of 33.32 percent carbon, 6.22 percent hydrogen, 21.49 percent nitrogen and 15.81 percent chlorine;
   (c) an infrared absorption spectrum in potassium bromide which exhibits peaks at the following wavenumbers in $cm^{-1}$: 3226, 1667, 1538, 1493 and 1227 as shown in FIG. 1;
   (d) a nuclear magnetic resonance spectrum (Fourier Transform) in deuterium oxide which exhibits the following chemical shifts in ppm: 8.3, 5.55, 5.2, 4.65 (m), 4.1 (t), 3.65 (d), 3.35, 3.05 and 2.1 as shown in FIG. 2;
   (e) an ultraviolet absorption spectrum in water which exhibits an absorption maximum at 267 nm and an absorption minimum at 230 nm as shown in FIG. 3;
   (f) a specific rotation $[\alpha]_D^{25} = -22.2°$ (C, 1.0 in $H_2O$); and
   (g) positive reactions with ninhydrin, molybdate, and permanganate and a negative reaction with periodate or a pharmaceutically acceptable salt thereof.

2. A polynitroxin antibiotic according to claim 1 which is in the form of the hydrochloride salt.

3. A process for the manufacture of the polynitroxin antibiotic of claim 1 which comprises culturing *Nocardiopsis mutabilis* Shearer sp. nov. ATCC 31520 in an aqueous nutrient medium containing assimilable sources of nitrogen and carbon under submerged aerobic conditions until a substantial amount of the antibiotic is produced and isolating the antibiotic so produced.

4. A process according to claim 3 wherein the isolation is accomplished by chromatographic means.

5. A process according to claim 3 wherein the culturing of the microorganism occurs at a temperature of 20° to 45° C.

6. A process according to claim 5 wherein the temperature is from 20° to 32° C.

7. A process according to claim 5 wherein the temperature is about 28° C.

8. A process according to claim 3 wherein the culturing of the microorganism continues from about 3 to about 7 days.

9. An antibacterial composition composition comprising an antibacterial effective amount of a polynitroxin antibiotic according to claims 1 or 2 and a pharmaceutically acceptable carrier.

* * * * *

UNITED STATES PATENT AND TRADEMARK OFFICE
CERTIFICATE OF CORRECTION

PATENT NO. : 4,317,812

DATED : March 2, 1982

INVENTOR(S) : Tikam C. Jain

It is certified that error appears in the above—identified patent and that said Letters Patent is hereby corrected as shown below:

On the first page of the patent, in the left-hand column, in item [75], the inventors should read -- Tikam C. Jain, King of Prussia; David J. Newman, Wayne; Marcia C. Shearer, Conshohocken; all of Pa. --.

Signed and Sealed this

Eighteenth Day of May 1982

[SEAL]

Attest:

Attesting Officer

GERALD J. MOSSINGHOFF

Commissioner of Patents and Trademarks